(12) United States Patent
Sinha et al.

(10) Patent No.: US 7,759,527 B2
(45) Date of Patent: Jul. 20, 2010

(54) MICROWAVE INDUCED ONE POT PROCESS FOR THE PREPARATION OF ARYLETHENES

(75) Inventors: Arun Kumar Sinha, Palampur (IN); Anuj A Sharma, Palampur (IN); Vinod Kumar, Palampur (IN)

(73) Assignee: Council of Scientific & Industrial Research, New Delhi (IN)

( * ) Notice: Subject to any disclaimer, the term of this patent is extended or adjusted under 35 U.S.C. 154(b) by 276 days.

(21) Appl. No.: 11/691,896

(22) Filed: Mar. 27, 2007

(65) Prior Publication Data

US 2008/0045752 A1 Feb. 21, 2008

(30) Foreign Application Priority Data

Mar. 28, 2006 (IN) .......................... 846/DEL/2006

(51) Int. Cl.
*C07C 41/01* (2006.01)
*C07C 37/00* (2006.01)
*C07C 67/00* (2006.01)

(52) U.S. Cl. ........................ 568/646; 568/650; 568/651; 568/652; 568/654; 568/716; 568/749; 568/766; 568/774; 568/780; 560/254

(58) Field of Classification Search ........................ None
See application file for complete search history.

(56) References Cited

U.S. PATENT DOCUMENTS 4,022,842 A * 5/1977 Hashimoto et al. .......... 568/644
7,220,784 B2 * 5/2007 Hadfield et al. ............. 514/749

OTHER PUBLICATIONS

Computer generated English translation, abstract and claims of JP 2004-231524, published Aug. 2004.*
Larhed et al., Microwave-assisted high-speed chemistry: a new technique in drug discovery, DDT, vol. 6, No. 8, Apr. 2001, pp. 406-416.*
Kuhnert, Microwave-Assisted Reactions in Organic Synthesis—Are There Any Nonthermal Microwave Effects?, Angew. Chem. Int. Ed. vol. 41, No. 11, Jun. 2002, pp. 1863-1866.*
Roberti et al., Synthesis and Biological Evaluation of Resveratrol and Analogues as Apoptosis-Inducing Agents, J. Med. Chem., vol. 46, No. 16, Jul. 2003, pp. 3546-3554.*
Dale et al., Substituted Styrenes. III. The Syntheses and Some Chemical Properties of the Vinylphenols, J. Am. Chem. Soc., Mar. 1958, vol. 80, No. 14, pp. 3645-3649.*

* cited by examiner

*Primary Examiner*—Rosalynd Keys
(74) *Attorney, Agent, or Firm*—Frank H. Foster; Kremblas & Foster

(57) ABSTRACT

The invention entitled "A Microwave Induced One Pot Process for The Preparation of Arylethenes" provides a method for the preparation of commercially important 2- or 4-hydroxy substituted arylethenes like styrenes or stilbenes in one pot utilizing cheaper substrates in the form of 2- or 4-hydroxy substituted cinnamic acids and their derivatives as well as reagents in the form of base such as sodium hydroxide, potassium hydroxide, lithium hydroxide, sodium bicarbonate, sodium carbonate, potassium bicarbonate, potassium carbonate, ammonium acetate, imidazole, methylimidazole and the combination thereof, with or without solvent such as dimethylformamide, dimethylsulfoxide, ethylene glycol, diethylene glycol, acetonitrile, acetone, methyl imidazoles, ionic liquid, water and the like. The reaction time vary from 1 min-12 hrs and yield of the products from 49-76% depending upon the base, acid, substrate source of heating monomode or multimode microwave or conventional. It is important to mention that the presence of 2- or 4-hydroxy substitution at phenyl ring of cinnamic acids and their derivatives is essential requirements towards formation of corresponding arylethenes in one step.

14 Claims, 5 Drawing Sheets

¹H NMR (300 MHz) Spectra in CDCl₃ 4-hydroxy-3-methoxy styrene $^{13}$C NMR (75.4 MHz) Spectrum in CDCl$_3$ -4-hydroxy-3-methoxy styrene $^1$H NMR (300 MHz) Spectra (in $CDCl_3$)-4-hydroxy-4'-dimethoxy $^{13}$C NMR (75.4 MHz) Spectrum (in $CDCl_3$)-4-hydroxy-3,4'-dimethoxy stilbene

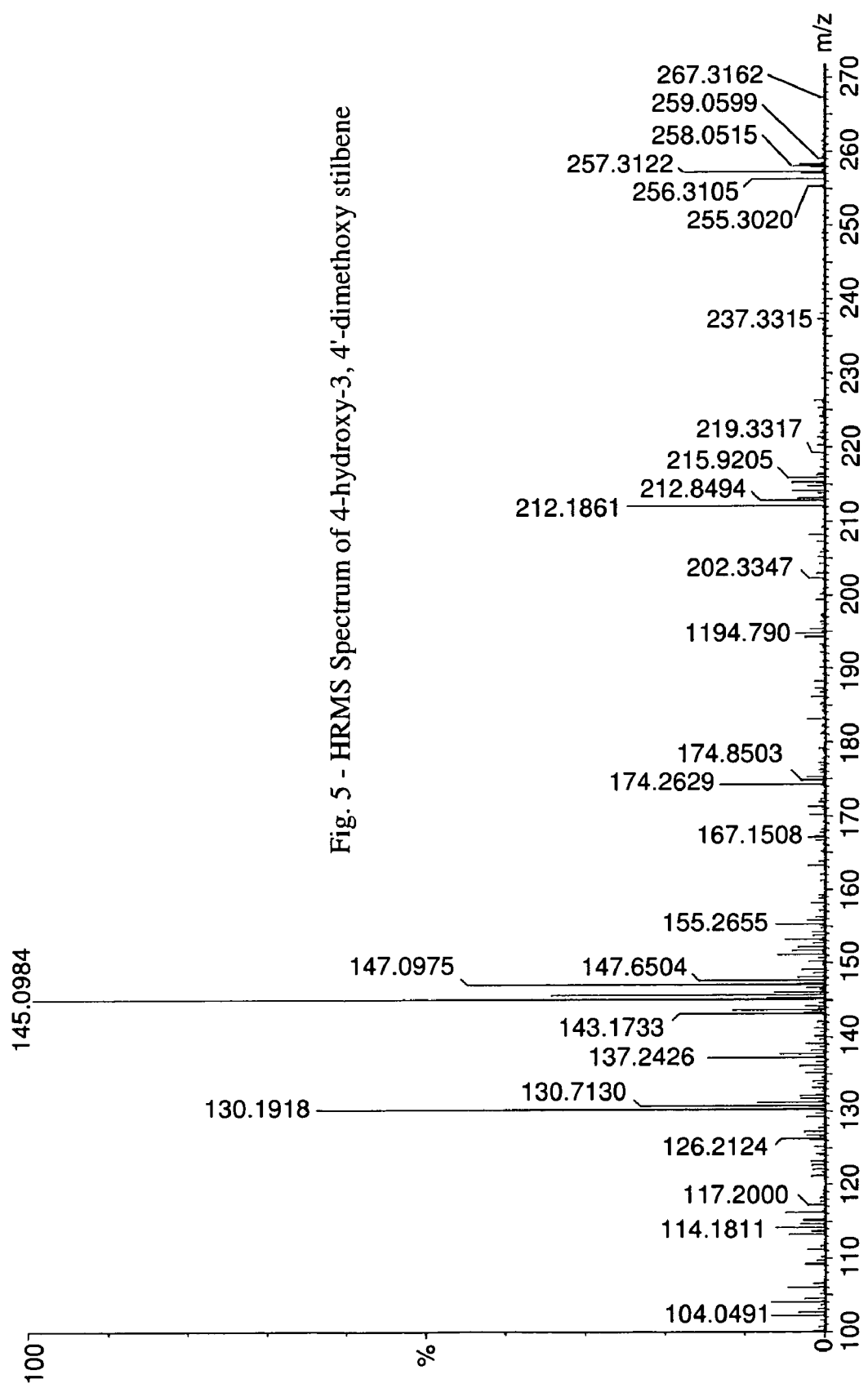
Fig. 5 - HRMS Spectrum of 4-hydroxy-3, 4'-dimethoxy stilbene

MICROWAVE INDUCED ONE POT PROCESS FOR THE PREPARATION OF ARYLETHENES

FIELD OF THE INVENTION

The present invention relates to a microwave induced one pot process for the preparation of arylethenes wherein, some immensely important arylethenes including various pharmacologically important stilbenes such as resveratrol (3,4',5-trihydroxy-(E)-stilbene) and pterostilbene (4-hydroxy-3',5'-dimethoxy stilbene) and styrenes like FEMA GRAS (Food Extract Manufacturer Association; Generally Regarded As Safe) approved 4-vinylguaiacol (FEMA GRAS No. 2675), 4-vinylphenol (FEMA GRAS No. 3739) are synthesized in one pot during decarboxylation of 2- or 4-hydroxy substituted cinnamic acids and their derivatives, using a base, solid support, with or without a solvent within minutes to hours under microwave irradiation or conventional heating in moderate to high yield. Cinnamic acids and their derivatives are selected from a group consisting of substituted cinnamic acids or α-phenyl cinnamic acids or cinnamic acid esters with at least one hydroxyl or alkoxy substitution at 2- or 4-position of aromatic ring and the like. The base for this process is selected from a group consisting of sodium hydroxide, potassium hydroxide, lithium hydroxide, sodium bicarbonate, sodium carbonate, potassium bicarbonate, potassium carbonate, ammonium acetate, imidazole, methylimidazole and the combination thereof. The solid support is selected from a group consisting of a basic alumina, acidic alumina, neutral alumina, silica gel and the like or the solvent is selected from a group consisting of dimethylformamide, dimethylsulfoxide, ethylene glycol, diethylene glycol, acetonitrile, acetone, methyl imidazoleas, ionic liquid, water and the like. The reaction time varies from 1 min to 12 hrs depending upon the solid support, solvents, substrate used, and source of monomode or multimode microwave used or conventional heating. Yield varies from 49-96% depending upon the substrate, base, solid support, and the solvent used. In addition, we disclose that the presence of hydroxy substitution at 2- or 4-position of the aromatic ring of cinnamic acid and its derivative is an essential requirement towards formation of arylethenes in one step. When reactions were performed with substrate where the starting material is not substituted by a hydroxy function at 2- or 4-position of aromatic ring the products were obtained in low yield. In the present invention, the formation of 2- or 4-hydroxy substituted arylethenes like stilbenes or styrenes, is the first example from corresponding protected or unprotected 2- or 4-hydroxy/acytyloxy substituted cinnamic acids and their derivatives without use of any decarboxylating agent and utilizing economical reagents and environment friendly microwave.

BACKGROUND OF THE INVENTION

Stilbenes based compounds are immensely important in the field of medicines and hydroxylated stilbenes have been found in a multitude of medicinal plants. (J. C. Roberts, J. A. Pincock, *J. Org. Chem.*, 2006, 71, 1480) For example, resveratrol, a hydroxylated stilbene, present in grapes and other fruits (J. Burns, T. Yokota, H. Ashihara, M. E. J. Lean, A. J. Crozier, *J. Agric. Food Chem.*, 2002, 50, 3337; G. J. Soleas, E. P. Diamandis, D. M. Goldberg, *Clin. Biochem.*, 1997, 30, 91) have been reported to play a role in the prevention of heart diseases associated with red wine consumption because of its properties of platelet aggregation (C. R. Pace-Asciak, S. Hahn, E. P. Diamandis, G. Soleas, D. M. Goldberg, Clin. Chem. Acta., 1995, 235, 207); eicosanoid synthesis alteration (Y. Kimura, H. Okuda, S. Arichi, *Biochim. Biophys. Acta.*, 1985, 834, 275), lipid and lipoprotein metabolism modulation (L. Belguendouz, L. Fremont, M. T. Gozzellino, *Biochem. Pharmacol.*, 1998, 55, 811; E. N. Frankel, A. L. Waterhouse, J. E. Kinsella, *Lancet.*, 1993, 341, 1103). Similarly, other hydroxy substituted stilbenes also have profound applications in the medicinal field (A. M. Rimando, M. Cuendet, C. Desmarchelier, R. G. Mehta, J. M. Pezzuto, S. O. Duke, *J. Agric. Chem.*, 2002, 50, 3453). Similarly, styrene based compounds of natural origin have received tremendous thrust from chemists all over the world due to a plethora of its applications in different spheres of services to mankind such as to flavour and fragrance industries, pharmaceutical sector etc. Compounds like substituted 4-vinylphenols such as 4-vinylguaiacol (p-vinylguaiacol or 2-methoxy-4-vinylphenol or 4-hydroxy-3-methoxystyrene or 4-ethenyl-2-methoxyphenol), 4-hydroxystyrene (p-vinylphenol or 4-ethenylphenol), 3,5-dimethoxy-4-hydroxy styrene and others have been the most extensively investigated ones due to their widespread application in food and alcoholic beverages, flavouring substances and as intermediates in the preparation of polymers and co-polymers useful in coatings, electronic applications, ion exchange resins and photo resists etc. (Perfume and Flavor Chemicals, Aroma Chemicals, ed. A. Steffen, Allured Publishing Corporation, 1994, Vol I-IV and *Encyclopedia of Food and Color Additives*, ed. A. B. George, CRC Press, Inc., 1996, Vol I-II).

The preparation of these substituted 2- or 4-hydroxy stilbene or styrene derivatives such as combretastatin A-4, reserveratrol, 4-vinylguaiacol (FEMA GRAS No. 2675), 4-vinylphenol (FEMA GRAS No. 3739) and others are well known in the art. However, a more efficient process for preparing 2- or 4-hydroxyl substituted arylethenes is desired. The present invention, which is an extension of our previous patent (U.S. Pat. No. 6,989,467, 2006), provides a process wherein microwave assisted (A. K. Bose, B. K. Banik, N. Lavlinskaia, M. Jayaraman, M. S. Manhas, *Chemtech.*, 1997, 27, 18; M. Larhed, Hallberg, *Drug Discovery Today.*, 2001, 6(8), 406,) decarboxylation of 2- or 4-hydroxy substituted cinnamic acids and their derivatives in the presence of a base, solid support with or without a solvent to provide corresponding substituted 2- or 4-hydroxy arylethenes in one pot. The following prior art references are disclosed:

U.S. Pat. No. 6,468,566 discloses a method for decarboxylation of ferulic acid with decarboxylase enzyme.

U.S. Pat. No. 6,235,507 discloses a method for decarboxylation of ferulic acid from microbial conversion at a pH more than 9.

U.S. Pat. No. 5,493,062 discloses a method for the preparation of styrenes from deamination of the corresponding aminoethylphenol (AEP) at high temperature.

U.S. Pat. No. 5,087,772 discloses a method for the preparation of styrenes from deacetoxylation of the corresponding acetoxystyrene with a suitable alcohol in the presence of a suitable base.

U.S. Pat. No. 20040147788 discloses a method for the synthesis of stilbene derivatives through Wittig reaction.

U.S. Pat. No. 20040015020 A1 discloses a method for the synthesis of E-isomer of stilbene through halide assisted conversion of corresponding Z-isomer.

*Journal of Biotechnology*, 2000, 80, 195; discloses a method for the preparation of 4-vinylguaiacol from decarboxylation of ferulic acid by *Bacillus coagulants*.

*Enzyme and Microbial Technology*, 1998, 23, 261; discloses a method for the decarboxylation of ferulic acid by *Bacillus pumilus*.

*Archives of Biochemistry and Biophysics,* 1998, 359(2), 225; discloses a method for the decarboxylation of hydroxycinnamic acid by *Klebsiella oxytoca.*

*J. Biol. Chem.,* 1993, 268, 23954; discloses a method for decarboxylation of cinnamic acid by *Rhodotorula rubra.*

*Appl. Environ. Microbial.,* 1993, 59, 2244; discloses a method for the decarboxylation of ferulic acid by *Saccharomyces cerevisiae* and *Pseudomonas fluorescens.*

*J. Biol. Chem.,* 1962, 237, 2926; discloses a method for the decarboxylation of 4-hydroxy-cinnamic acid by Aerobacter.

*Tetrahedron.,* 2004, 60, 5563; discloses a method for the synthesis of resveratrol and their analogues through Heck reaction in organic and aqueous solvents.

*Journal of Med. Chem.,* 2002, 45, 2534; discloses a method for the synthesis of hydroxy stilbenes and benzophenones through Wittig reaction.

*J. Biol. Chem.,* 1961, 236, 2302; discloses a method for the decarboxylation of trans-cinnamic acids into styrene derivatives by using pyruvate decarboxylase enzyme.

*J. Biol. Chem.,* 1957, 227, 151; discloses a method for the decarboxylation of trans-cinnamic acids into styrene derivatives by using oxalate decarboxylase enzyme.

*J. Biol. Chem.,* 1960, 235, 1649; discloses a method for the decarboxylation of trans-cinnamic acids into styrene derivatives by using glutamate decarboxylase enzyme.

*J. Biol. Chem.,* 1957, 226, 703; discloses a method for the decarboxylation of trans-cinnamic acids into styrene derivatives by using aconitate decarboxylase enzyme.

*J. Biol. Chem.,* 1964, 239, 879; discloses a method for the decarboxylation of trans-cinnamic acids into styrene derivatives by using aspartate 4-decarboxylase enzyme.

*Natural Product Research.,* 2006, 20, 247, discloses a method for the improve synthesis of resveratrol through two step process Wittig reaction and Heck coupling.

*Synthesis,* 2006, 273, discloses a method for the synthesis of biologically important trans-stilbenes via Ru-catalyzed cross metathesis.

*J. Med. Chem.,* 2005, 48, 6783, discloses a method for the synthesis resveratrol analogue with high ceramide-mediated proapoptotic activity on human breast cancer cells.

*Carbohydrate Research.,* 1997, 301, 95; discloses a method for the synthesis of various hydroxy stilbenes and their glycosides through Wittig reaction.

*Tetrahedron Lett.,* 1999, 40, 6595; discloses a method for the decarboxylation of trans-cinnamic acids into styrene derivatives by using plant cell cultures.

*J. Biol. Chem.,* 1962, 237, 2926; discloses a method for the decarboxylation of trans-4-hydroxycinnamic acid into 4-hydroxystyrene.

*Applied Catalyst A: General,* 1995, 133, 219; discloses a method for the preparation of styrene from dehydrogenation of ethylbenzene.

*Organic Synthesis Collective* Volume 1, 1941, 441-442 as well as Volume IV, 1963, 731-734; disclose a method for the preparation of styrenes by decarboxylation of cinnamic acids with quinoline in the presence of copper powder at 200-300° C.

Some of other typical prior art references include U.S. Pat. Nos. 4,316,995; 4,868,256; 4,868,257; 4,933,495; 5,072,025; 5,128,253; 5,247,124; 5,344,963; 5,563,289; 6,111,133; European Pat. Nos. 0-128-984; 0-108-624; Dutch Pat. Nos. 72.09426; 72.13842; 75.04532; Japan Pat. Nos. 10306126; 6049137; *J. Am. Chem. Soc.,* 1948, 70, 2295; *J. Am. Chem. Soc.,* 1950, 72, 5198; *J. Am. Chem. Soc.,* 1958, 80, 3645; *J. Org. Chem.,* 1958, 23, 544; *Chem. Berichte,* 1959, 92, 2958; *Tetrahedron,* 1975, 31, 235; *Can. J. Chem.,* 1985, 63, 153.

Although, the above methods have been proven to be useful, they suffer from one or more process deficiencies. For example, in some instances processes of this type necessarily involve resorting to sub-ambient temperatures and in some others, the substrates require designing of multi-step processes which of course, involve some considerable process control and leads to overall poor yield of the products.

Natural plant products represent one of the important branches of organic chemistry which serves mankind to satiate his wide range of necessities for food, perfumery, and pharmaceutical industries etc. Naturally occurring non-nutritive agents such as flavonoids, phenolic compounds, styrenes, stilbenes and many others are believed to possess varied pharmacological activities (S. M. Kau, *Oncogenesis,* 1997, 8, 47) whose clinical relevance is dependent on extrapolation from epidemiological data. For example, hydroxylated stilbenes, a class of phenolic compounds, includes one of the most important therapeutic agents like combretastatin A-4, pterostilbene and resveratrol for the prevention of fatal diseases like cancer and heart diseases. Combretastatin A-4, isolated from the African bush willow, *Combretum caffrum* shows exciting potential as an anti-cancer agent, binding strongly to tubulin and displaying potent and selective toxicity towards tumor vasculature (U.S. Pat. No. 4996; *Brit. J. Cancer,* 1999, 81, 1318; *Brit. J. Cancer,* 1995, 71, 705). Combretastatin A-4 is able to elicit irreversible vascular shutdown within solid tumors, leaving normal vasculature intact (E. Hamel, C. M. Lin, *Biochem. Pharmacol.,* 1983, 32, 3863; D. J. Chaplin, G. R. Pettit, C. S. Parkins, S. A. Hill, *Brit. J. Cancer,* 1996, 74, S86; G. G. Dark, S. A. Hill, V. E. Prise, G. M. Tozer, G. R. Pettit, D. J. Chaplin, *Cancer Res.* 1997, 57, 1829). Similarly, resveratrol, a natural molecule, occuring in a narrow range of spermatophytes, including vines, peanuts and pine trees, is known to prevent heart disease. The compound is shown to be bioactive (C. A. De La Lastra, I. Villegas, *Molecular Nutrition and Food chemistry,* 2005, 49, 405; S. H. Inayat-Hussain, N. F. Thomas, *Expert Opin. Ther. Pat.,* 2004, 14, 819; F. Wolter, J. Stein, *Drugs Future,* 2002, 27, 949; Y. Kimura, H. Okuda, S. Arichi, *Biochim. Biophys. Acta,* 1985, 834, 275; L. A. Stivala, M. Savio, F. Carafoli, P. Perucca, L. Bianchi, G. Maga, L. Forti, U. M. Pagoni, A. Albini., E. Prosperi, V. Vannini, *J. Boil. Chem.,* 2001, 176, 22586; Y. Schneider, B. Duranton, F. Gossé, R. Schleiffer, N. Seiler, F. Raul, *Nutr. Cancer,* 2001, 39, 102; M. Chung, C. Teng, K. Cheng, F. Ko, C. Lin, *Planta Med.,* 1992, 58, 274; Y. Inamori, M. Kubo, H. Tsujibo, M. Ogawa, Y. Saito, Y. Miki, S. Takemura, *Chem. Pharm. Bull.,* 1987, 35, 887). Its synthesis in the plants is induced by stress, including infection or UV-irradiation. High concentrations of this compound have been isolated from the plant *Poligonum cuspidatum.* Resveratrol is shown to inhibit synthesis of thromboxnae in platelets and leukotrienes in neutrophils, and modulate the synthesis and secretion of lipoproteins in animals and human cell lines and thus, significantly prevent coronary diseases. Moreover, resveratrol prevents chemical induction of preneoplastic lesion in a mouse mammary gland culture model and can slowdown the growth of skin tumors. It is shown that resveratrol can protect against a variety of diseases associated with AhR ligand. Hence, resveratrol acts as AhR antagonist and thus helps preventing cancer and viral infections such as AIDS (K. W. Bock, *Physiol, Biochem. Pharmacol.,* 1994, 125, 1; J.-F. Savouret, M. Antenos, M. Quesne, J. Xu, E. Milgrom, R. F. Casper, *J. Boil. Chem.,* 2001, 276, 3054; M. Poirot, P. De Medina, F. Delarue, J. J. Perie, A. Klaebe, J. C. Faye, *Bioorg. Med. Chem.,* 2000, 8, 2007). This compound is also known to possess anti-inflammatory and anti-mutagebnic activities. (*Science,* 1995, 267, 1782; *Science,* 1997, 275, 218). Similarly, natural vinylphenols, another class of important styrene derivatives, are immensely important constituents for aroma and flavor industries and are found in a variety of plant products. For example, vinylguaiacol (FEMA GRAS NO. 2675) is obtained from the pods of *Hibiscus esculentus* (okra) and *Digitaria exilis* and also found in cooked apple, grape fruit juice (*Citrus paradisi*), feijoa fruit (*Feijoa sellowiana*), *Vitis vinifera*, strawberry fruit, raw asparagus, leaves and stalks of celery, crispbread, white wine, red wine, coffee, partially fermented tea, roasted peanuts (*Arachis hypogea*), raw beans, red sage (*Taxus sage*) and other natural sources (M. A. Jennifer, M. Glesni, *Phytochemistry*, 1990, 29 (4), 1201; P. Hanna, N. Michael, Z. Uri, L. R. Russell, N. J. Steven, *J. Agric. Food Chem.*, 1992, 40, 764; O. O. Lasekan, J. P. F. Teixeira, T. J. G. Salva, *Food Chemistry*, 2001, 75, 333). 4-vinylguiacol is also found as one of the most odour active compounds in roasted white sesame seeds which are widely used as a flavouring material in food stuffs. (Progress In Flavour Precursor Studies, ed. P. Schreier, P. Winterhalter, Allured Publishing Corporation, USA, 1993, 343-360; W. Toshiro, Y. Akira, N. Shiro, T. J. Shigero, *J. Chromatogra. A*, 1998, 3, 409). On the same lines, 4-vinylphenol, also known as 4-hydroxystyrene, (FEMA GRAS NO. 3739) is found in cooked apple, black currants (buds), raw asparagus, tomato, cognac, white wine, red wine, rose wine, coffee, green tea, partially fermented tea, microbial fermented tea, heated soyabean, *Boletus edulis*, coriander seed (*Coriandrum sativum*), oil of vetiver (*Vetiveria zizamioides*), olive oil and other natural sources (S. Souleymane, C. Jean, *Phytochemistry*, 1973, 2925; S. Takayuki, N. Osamu, *Phytochemistry*, 1982, 1(3), 793; O. Makoto, W. Kazumasa, N. Haruki, Y. Kiyoyuki, *Tetrahedron*, 1987, 43(22), 5275; J. J. S. Saez, M. D. H. Garraleta, T. B. Otero, *Analytica Chimica Acta*, 1991, 247(2), 295; F. Vicente, L. Ricardo, E. Ana, F. C. Juan, *J. Chromatogar. A*, 1998, 806, 349; J. W. Nicholas, N. Arjan, B. F. Craig, W. Gray, *Current Opinion in Biotechnology*, 2000, 11, 490; P. Rainer, S. Alexander, P. Horst, *FEMS Microbiology Letters*, 2001, 205, 9; L. Ricardo, A. Margarita, C. Juan, F. Vicente, *J. Chromatogra. A*, 2002, 966, 167; K. Kuroda, D. R. Dimmel, *J. Analytical and Applied Pyrolysis*, 2002, 62, 259; K. Kuroda, A. Izumi, B. B. Mazumder, Y. Ohtani, K. Sameshima, *J. Analytical and Applied Pyrolysis*, 2002, 64, 453; F. Daniel, V. Ivano, E. S. Colin, *J. Chromatogra. A*, 2002, 967, 235). In addition to the above mentioned vinylphenols, there are several other styrenes which are found in different plants and are known for various applications. (F. Nagashima, Y. Murakami, Y. Asakawa, *Phytochemistry*, 1999, 51, 1101). Beside, vinylphenols are also known to possess a wide range of biological activities including antibacterial, antifungal and hypolipidemic activities etc. (A. A. William, J. M. David, C. Priyotosh, *Phytochemistry*, 1996, 42(5), 1321; C. Adriana, G. Leticia, S. Maria, M. Elizdath, A. J. Hugo, D. Francisco, C. Germán, T. Joaquin, F. Arzneim, *Drug Res.*, 2001, 51(II), 535). In addition to above, vinylphenols and related styrenes are also found as versatile intermediates for a wide range of products (R. R. Stuart, S. M. Colette, J. L. David, *Biorganic & Medicinal Chemistry*, 1994, 2(6), 553; M. Atsushi, K. Takeo, I. Yoshinobu, *Reactive & Functional Polymers*, 1998, 37, 39; C. B. Michel, L. M. Adriano, T. Igor, *J. of Molecular Catalyst A: Chemical*, 1999, 143, 131; J. C. Pedro, G. Bárbara, A. R. Miguel, *Tetrahedron Lett;* 2000, 41, 979).

In the pretext of above discussion, 2- or 4-hydroxy substituted arylethenes like stilbenes and styrenes can unhesitatingly be counted as greatly valued to humankind and as a consequence, a lot of synthetic methods are reported for their synthesis. In case of synthesis of stilbene derivatives, the reported methods involve Wittig type and modified Julia olefination, reaction of benzyllithium with benzaldehydes followed by dehydration, Perkins reaction, cross metathesis of styrenes, Suzuki reaction with B-halostyrenes, decarbonylative Heck reaction between acid chloride and styrene and palladium catalysed arylation of styrenes with halobenzene (G. R. Pettit, M. P. Grealish, M. K. Jung, E. Hamel, R. K. Pettit, J.-C. Chapuis, J. M. Schmidt, *J. Med. Chem.*, 2002, 45, 2534; M. Roberti, D. Pizzirani, D. Simony, R. Rondanin, R. Baruchello, C. Bonora, F. Buscemi, S. Grimaudo, M. Tolomeo, *J. Med. Chem.*, 2003, 46, 3546; H. Meier, U. Dullweber, *Tetrahedron Lett.*, 1996, 37, 1191; J. Yu, M. J. Gaunt, J. B. Spencer, *J. Org. Chem.*, 2002, 67, 4627; D. A. Alonso, C. Nájera, M. Varea, *Tetrahedron Lett.*, 2004, 45, 573; E. Alonso, D. J. Ramón, M. Yus, *J. Org. Chem.*, 1997, 62, 47; G. Solladié, Y. Pasturel-Jacopé, J. Maignun, *Tetrahedron*, 2003, 59, 3315; S. Chang, Y. Na, H. J. Shin, E. Choi, L. S. Jeong, *Tetrahedron Lett.*, 2002, 43, 7445; S. Eddarir, Z. Abdelhadi, C. Rolando, *Tetrahedron Lett.*, 2001, 42, 9127; M. B. Andrus, J. Liu, E. L. Meredith, E. Nartey, *Tetrahedron Lett.*, 2003, 44, 4819; T. Jeffery, B. Ferber, *Tetrahedron Lett.*, 2003, 44, 193; N. F. Thomas, K. C. Lee, T. Paraidathathu, J. F. F. Weber, K. Awing, *Tetrahedron Lett.*, 2002, 43, 3151). Similarly, reported methods for the synthesis of vinyl phenols include decarboxylation of trans-cinnamic acids which is carried out by heating the cinnamic acids under reflux at 200-300° C. for several hours in quinoline in the presence of copper powder (Organic Synthesis Collective Volume I, 1941, 441-442 and Volume IV, 1963, 731-734; A. S. Robert, R. D. Charles, A. P. Leo, *Tertrahedron Lett.*, 1976, 49, 4447). Similarly, catalytic oxidation of 1,1-diphenylethane (1,1-di-(4-hydroxyphenyl) ethane) provides styrene (i.e. 4-hydroxy-3-methoxystyrene) (Perfume and Flavor Chemicals (Aroma Chemicals), ed. Steffen, A., Allured Publishing Corporation, 1994, Vol II, 1891). In addition to chemical methods, several microbial transformations are also reported for the preparation of styrenes especially substituted vinylphenols (T. Masumi, A. Kazuo, *Tetrahedron Lett.*, 1999, 40, 6595; and Encyclopedia of Food and Color Additives, ed. George, A. B., CRC Press, Inc., Vol II, 1996, 705). All the above methods have various limitations, for example, low yield, use of expensive reagents and formation of unwanted side products.

It is therefore, becomes an object of the invention to provide rapid and economical process for the preparation of 2- or 4-hydroxy substituted arylethenes from commercially available 2- or 4-hydroxy substituted cinnamic acids and their derivatives as well as to eliminate the disadvantages associated with the above patents and papers.

In conclusion, our invention discloses a simple and economical process for preparing 2- or 4-hydroxy substituted arylethenes from economical material 2- or 4-hydroxy substituted cinnamic acids and their derivatives in the presence of a base, solid support with or without solvent under microwave or conventional condition. Other objectives and advantages of the present invention will be apparent as the description progresses.

OBJECTIVES OF THE INVENTION

The main object of the present invention is to prepare high valued 2- or 4-hydroxy substituted arylethenes like stilbenes or styrenes from corresponding cinnamic acids and their derivatives.

Yet another object of the invention is to develop a process in which cinnamic acids and their derivatives are selected from a group consisting of substituted cinnamic acids α-phenyl cinnamic acids or cinnamic acid esters with at least one hydroxyl substitution unprotected or protected by acetyl, benzyl groups and the like at 2- or 4-position of aromatic ring.

Yet another object of the present invention is to develop a process wherein the product 2- or 4-hydroxy substituted arylethenes is formed both under microwave irradiation as well as conventional heating.

Still another object of the invention is to develop a process in which the reaction can be performed under solvent less condition using solid support.

Yet another object of the present invention is to develop a process wherein microwave enhances the yield of product stilbenes as compared to conventional method.

Yet another object of the present invention is to develop a process which is found equally workable in monomode and multimode microwave.

Yet another object of the invention is to develop a process to prepare 2- or 4-hydroxy substituted arylethenes in one pot.

Yet another object of the invention is to develop a process in which some of catalyzing organic bases such as piperidine and acetic acid are approved by FEMA GRAS which makes our process even safer and eco-friendly.

Yet another object of the invention is to develop a process for easy workup as well as purification of the product.

Still another object of the invention is to develop a process which utilizes less hazardous or non-hazardous chemicals.

Still another object of the invention is to develop a process which requires cheaper chemical reagents.

Yet another object of the invention is to develop industrially viable process towards formation of high valued and medicinally important 2- or 4-hydroxy substituted arylethenes.

SUMMARY OF THE INVENTION

Accordingly, the present invention provides a process for the preparation of commercially important 2- or 4-hydroxy substituted arylethenes like styrenes such as 4-vinylguaiacol, 4-vinylphenol and 2- or 4-hydroxy substituted stilbenes such as resveratrol, combretastatin and many others in one pot under microwave irradiation utilizing economical substrates in the form of 2- or 4-hydroxy substituted cinnamic acids and their derivatives. Cinnamic acids and their derivatives are selected from a group consisting of substituted cinnamic acids or α-phenyl cinnamic acids or cinnamic acid esters with at least one hydroxyl or alkoxy substitution at 2- or 4-position of aromatic ring and the like. The base used is selected from a group consisting of sodium hydroxide, potassium hydroxide, lithium hydroxide, sodium bicarbonate, sodium carbonate, potassium bicarbonate, potassium carbonate, ammonium acetate, imidazole, methylimidazole and the combination thereof. The solid support is selected from a group consisting of a basic alumina, acidic alumina, neutral alumina, silica gel and the like. Wherever used, solvent is selected from a group consisting of dimethylformamide, dimethylsulfoxide, ethylene glycol, diethylene glycol, acetonitrile, acetone, methyl imidazoles, ionic liquid, water and the like. The final products i.e. 2- or 4-hydroxy substituted arylethenes were obtained in moderate to excellent yield varying from 49-96% within 1 min-12 hrs. It is worthwhile to mention that in this decarboxylation process, the presence of hydroxy substitution at 2- or 4-position of cinnamic acids and their derivatives is an essential requirement towards formation of corresponding arylethenes in one step under microwave or conventional conditions. It is also important to note that use of microwave irradiations enhances the yield of product as compared to conventional heating.

BRIEF DESCRIPTION OF THE ACCOMPANYING DRAWINGS

FIG. 5 is HRMS spectrum of 4-hydroxy-3,4'-dimethoxy stilbene. (Example III)

DETAILED DESCRIPTION OF THE INVENTION

Figure 1:
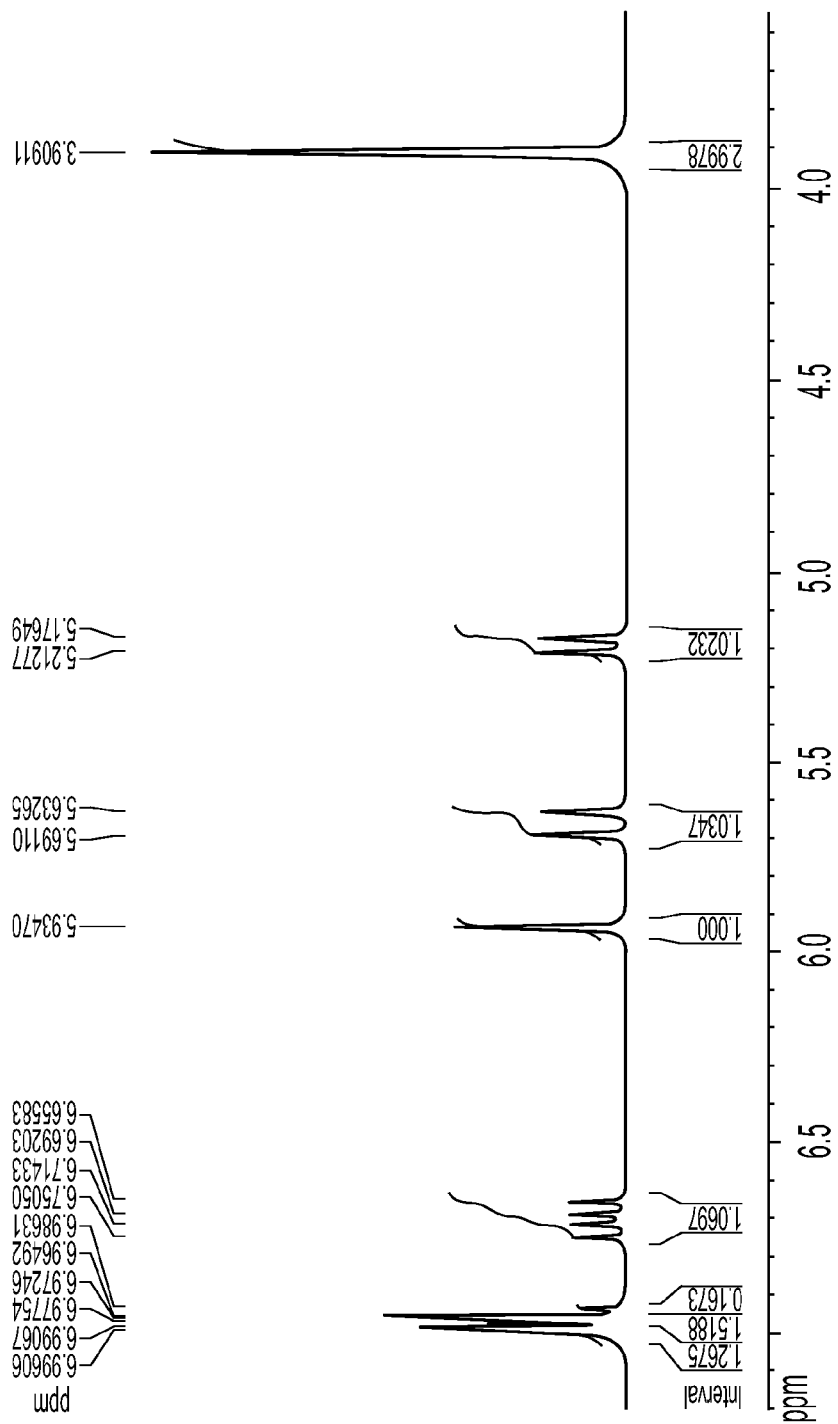
FIG. 1 is $^1$H NMR (300 MHz) spectra of vinylguaiacol (4-hydroxy-3-methoxy styrene) in CDCl$_3$. (Example I)
Figure 2:
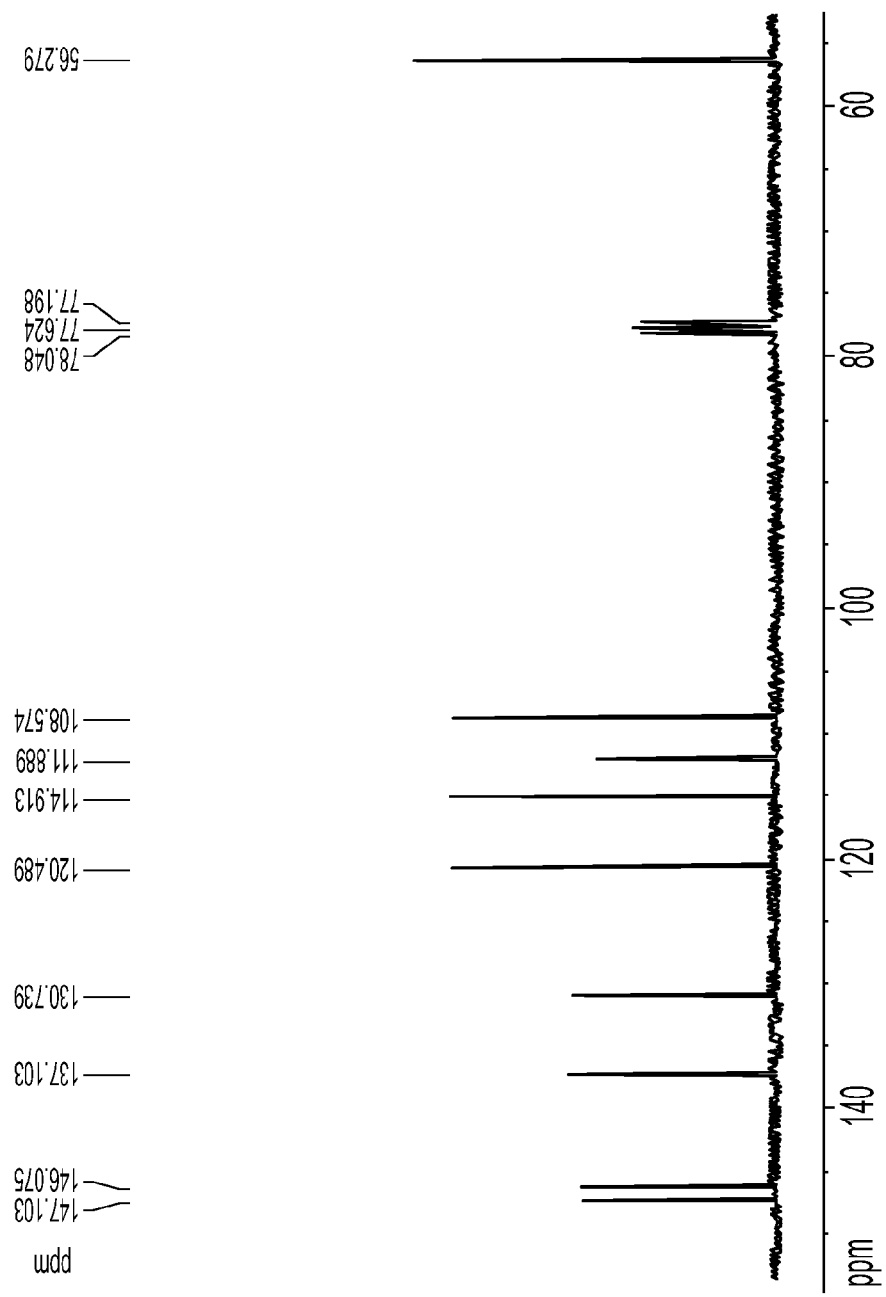
FIG. 2 is $^{13}$C NMR (75.4 MHz) spectra of vinylguaiacol (4-hydroxy-3-methoxy styrene) in CDCl$_3$ (Example I)
Figure 3:
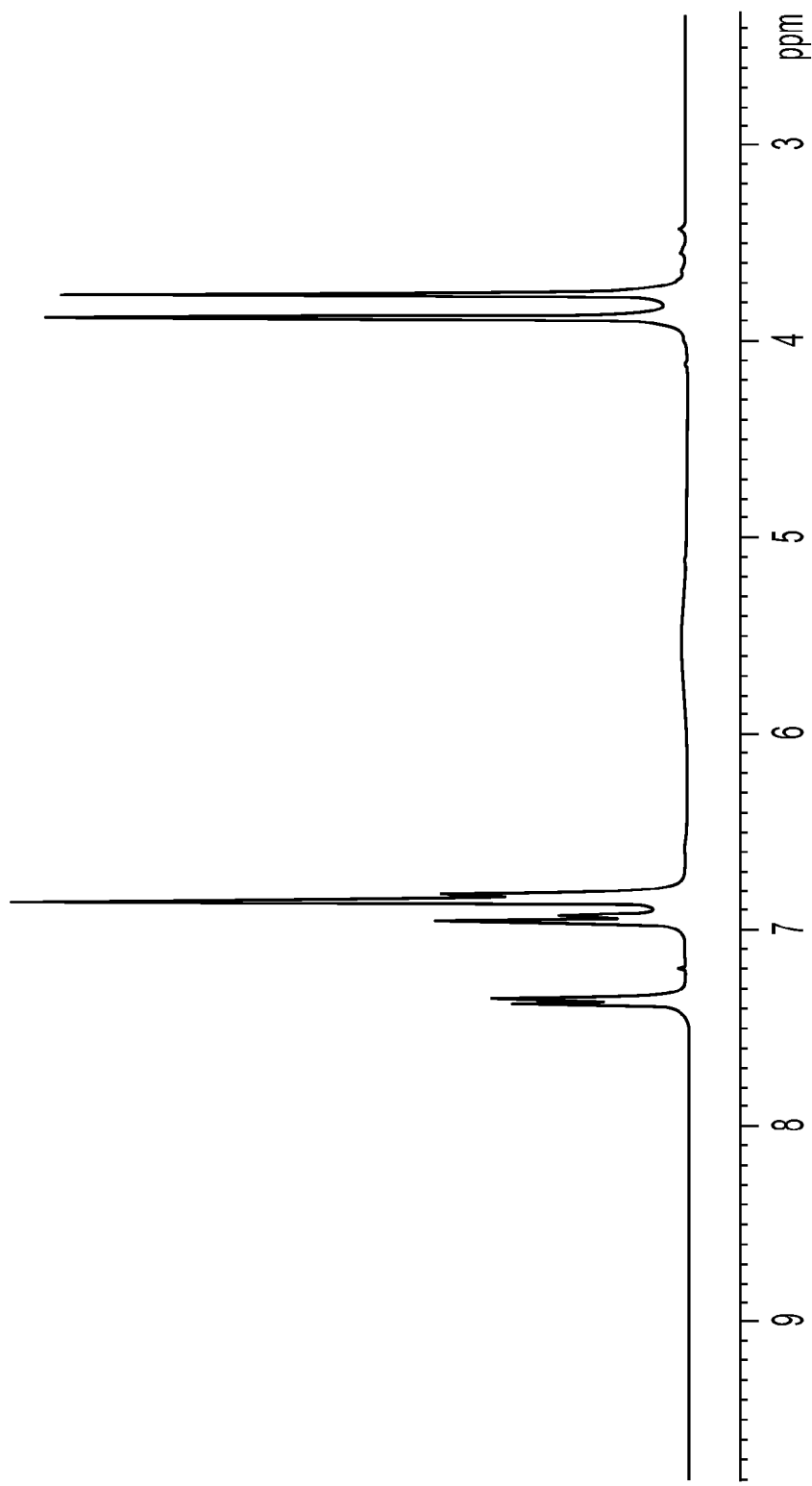
FIG. 3 is $^1$H NMR (300 MHz) spectra of 4-hydroxy-3,4'-dimethoxy stilbene in CDCl$_3$. (Example III)
Figure 4:
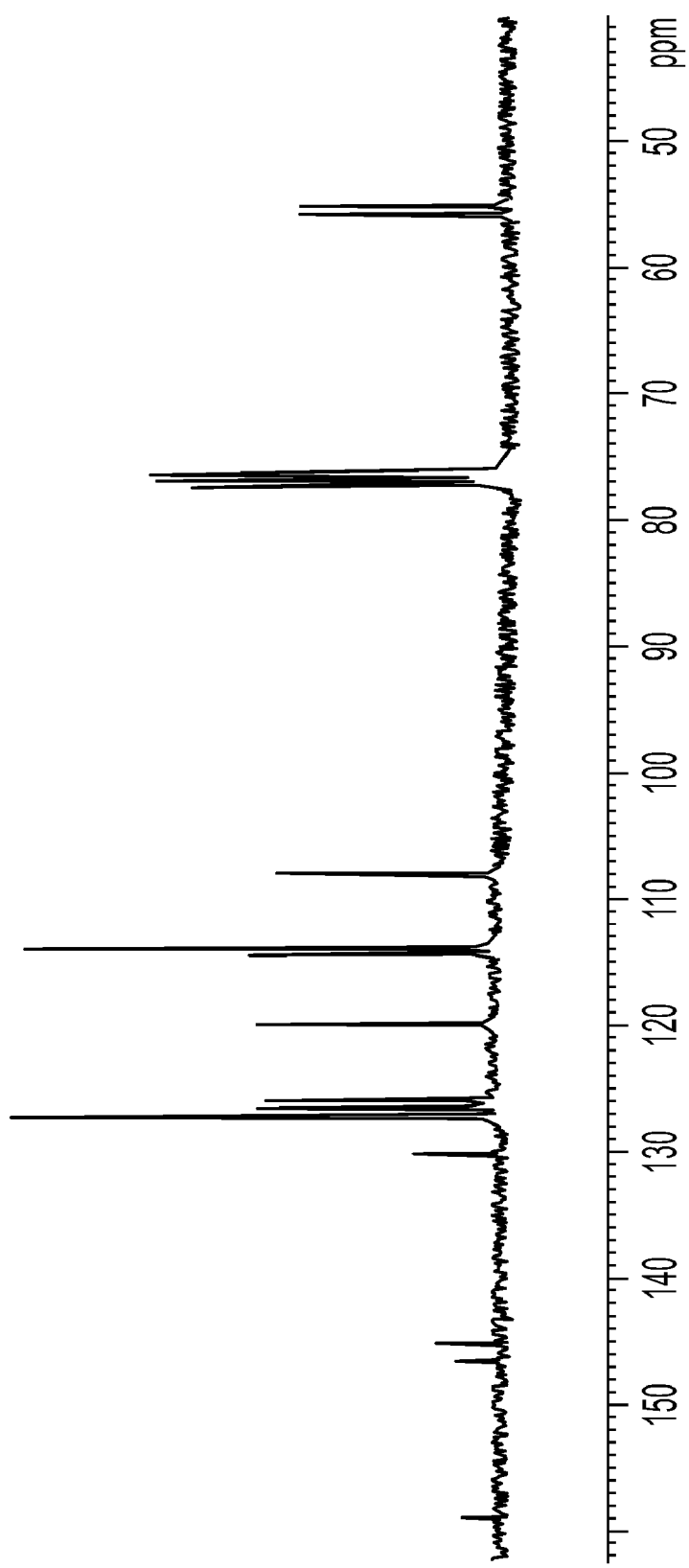
FIG. 4 is $^{13}$C NMR (75.4 MHz) spectra of 4-hydroxy-3,4'-dimethoxy stilbene in CDCl$_3$. (Example III)

Accordingly, the present invention provides a microwave induced one pot process for the preparation of arylethenes of general formula I

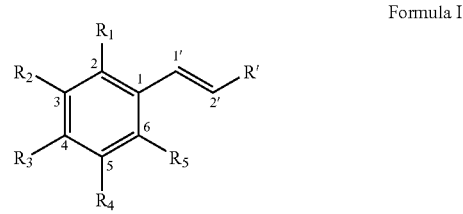

Formula I wherein R$_1$ to R$_5$ are defined as, at least one OH or acetoxy substituent among R$_1$, R$_3$, R$_5$ and rest of substituents R$_1$ to R$_5$, being H or OH or OCH$_3$ or CH$_3$COO— or halogen or nitro or combinations thereof, R'=H in case of styrenes and substituted aryl group in case of stilbenes, the said process comprising steps of:

a) reaction of 2- or 4-hydroxy substituted cinnamic acid or its derivative in the presence of a base, solid support, with or without solvent by refluxing or under microwave irradiation for 1 min-12 hrs, b) transferring the reaction mixture of step (a) and washing the residue with an organic solvent, c) washing the organic solution of step (b) with aqueous sodium bicarbonate or sodium carbonate followed by brine and water, d) drying the organic layer of step (c) over anhydrous sodium sulphate, filtering and evaporating to dryness to completely remove the solvent to obtain a residue, e) purifying the residue of step (d) by column chromatography or recrystallization to obtain the corresponding arylethenes of general formula (I).

In another embodiment of the present invention, wherein arylethenes like stilbenes or styrenes are prepared by decarboxylation of corresponding cinnamic acids and their derivatives.

In another embodiment of the present invention, wherein cinnamic acids and their derivatives are selected from a group consisting of substituted cinnamic acids or α-phenyl cinnamic acids or cinnamic acid esters with at least one hydroxyl substitution unprotected or protected by acetyl, benzyl groups at 2- or 4-position of aromatic ring.

In another embodiment of the present invention, wherein the products 2- or 4-hydroxy substituted arylethenes are formed both under microwave irradiation as well as with conventional heating.

In another embodiment of the present invention, wherein cinnamic acids and their derivatives are selected from a group consisting of substituted cinnamic acids or α-phenyl cinnamic acids or cinnamic acid esters with at least one hydroxyl substitution unprotected or protected by acetyl, benzyl groups and the like at 2- or 4-position of aromatic ring.

In another embodiment of the present invention, wherein base is selected from a group consisting of sodium hydroxide, potassium hydroxide, lithium hydroxide, sodium bicarbonate, sodium carbonate, potassium bicarbonate, potassium carbonate, ammonium acetate, imidazole, methylimidazole and the combination thereof.

In another embodiment of the present invention, wherein the combined effect of inorganic and organic bases enhanced the yield of product by 25-30%.

In another embodiment of the present invention, wherein the solid support is selected from a group consisting of a basic alumina, acidic alumina, neutral alumina, silica gel and the like.

In another embodiment of the present invention, wherein the solvent wherever used is selected from a group consisting of dimethylformamide, dimethylsulfoxide, ethylene glycol, diethylene glycol, acetonitrile, acetone, methylimidazoles, ionic liquid, water and the combination thereof.

In another embodiment of the present invention, wherein the process show remarkable selectivity for the decarboxylation of cinnamic acid moiety in comparison to benzoic acids, phenylacetic acids, phenylpropanoic acid and the like.

In another embodiment of the present invention, wherein the mole ratio between the 2- or 4-hydroxy substituted cinnamic acid and base is ranging from 1:1 to 1:20 moles, more preferably 1:3.

Yet another embodiment of the present invention, wherein the mole ratio between the 2- or 4-hydroxy substituted cinnamic acid and solid support is ranging from 1:1 to 1:50 moles, more preferably 1:5.

Yet another embodiment of the present invention, wherein the mole ratio between the 2- or 4-hydroxy substituted cinnamic acid and solvent wherever used is ranging from 1:1 to 1:10 moles, more preferably 1:5.

In yet another embodiment of the present invention, wherein the method is found equally workable in monomode and multimode microwave.

In yet another embodiment of the present invention, wherein the reaction is performed in a monomode microwave operated at 30 W-300 W power level with 80-250° C. for 1-20 min.

In another embodiment of the present invention, wherein the microwave irradiation frequency used is in the range of 900 to 3000 MHz, more preferably 2450 to 2455 MHz.

In another embodiment of the present invention, wherein the temperature attained in case of monomode microwave is ranging from 80-250° C., preferably 110-200° C.

In yet another embodiment of the present invention, wherein the reaction is successfully performed in a domestic multimode microwave oven operated at 700 W-1500 W power level for 1-20 min, more preferably 1-15 min.

In another embodiment of the present invention, wherein the reaction is also successfully performed by refluxing the substrates for 2-12 hrs, preferably 2-5 hrs.

In another embodiment of the present invention, wherein developed process is applied equally successfully on aryl acrylic acids containing aryl rings other than phenyl such as naphthyl, phenanthryl, pyridyl, indyl, furyl, thiazolyl ring and the like.

In yet another embodiment of the present invention, wherein the products were obtained in low yield when the starting material is not substituted by a hydroxy function at 2- or 4-position.

In yet another embodiment of the present invention, wherein ecofriendly, economical and industrial process is developed for the preparation of 2- or 4-hydroxy substituted arylethenes in moderate to high yield.

Keeping in view the problems, we disclose a unique and novel microwave-assisted process to prepare 2- or 4-hydroxy substituted arylethenes like styrenes or stilbenes (Examples I-V) in one step from decarboxylation of corresponding cinnamic acids in the presence of a base and an organic solvent. In fact, we have already observed that while trying to emulate Knoevenagel Doebner condensation (B. S. Furniss, A. J. Hannaford, V. Rogers, P. W. G. Smith, A. R. Tatchell; In: Vogel's Textbook of Practical Organic Chemistry, fourth Edn. (ELBS, UK), 1978, 802) reaction under microwave (A. K. Bose, B. K. Banik, N. Lavlinskaia, M. Jayaraman, M. S. Manhas, $Chemtech,$ 1997, 27, 18; M. Larhed, Hallberg, $Drug Discovery Today,$ 2001, 6(8), 406; C. Kuang, H. Senboku, M. Tokuda, $Tetrahedron,$ 2002, 58, 1491; N. Kuhnert, $Angew. Chem. Int Ed.,$ 2002, 41, 1863) 4-hydroxy substituted benzaldehydes produce styrenes instead of the expected cinnamic acids (A. K. Sinha, B. P. Joshi, A. Sharma, U.S. Pat. No. 6,989,467, 2006).

Initially, we employed the Perkin reaction between vanillin (4-hydroxy-3-methoxybenzaldehyde) and phenylacetic acid in presence of triethylamine and acetic anhydride to obtain the corresponding acetoxylated α-phenylcinnamic acid. Our subsequent quest for the development of a safe and efficient decarboxylation protocol for these acetoxylated α-phenylcinnamic acids prompted us to explore microwave coupled basic aqueous conditions in lieu of the prevalent toxic quinoline/copper salt mediated decarboxylation protocols. (A. F. Shepard, N. R. Winslow, J. R. Johnson, $J. Am. Chem. Soc.,$ 1930; 52, 2083) Decarboxylation under aqueous basic conditions offers several inherent advantages. Water is rapidly heated by microwave irradiation to high reaction temperatures which enables it to behave as a pseudo organic solvent. In this light, we hypothesized that water might also help stabilize the transition state/intermediate(s) in the base induced decarboxylation of α-phenylcinnamic acids. We further reasoned that the coupling of aqueous basic conditions with an efficient energy source like microwave might help drive the reaction kinetic past the transition barrier to provide stilbenes from the corresponding acetoxylated α-phenylcinnamic acids.

In order to test this hypothesis, a mixture of α-phenyl-4-acetoxy-3-methoxycinnamic acid (1a) and 10% aqueous sodium bicarbonate solution was irradiated under microwave for 20 min. It was indeed a delight to observe the corresponding (E)-stilbene 1b albeit in 18% yield along with the deacetylated α-phenyl-4-hydroxy-3-methoxycinnamic acid. The partial success inspired us to devise further modifications in our protocol. We realized that the low yield of stilbene might in part be attributed to the inability of low boiling aqueous solution to attain temperatures appropriate for decarboxylation. Thereafter, a number of high boiling solvents (DMF, DMSO, EG, PEG) were screened for the above reaction and 10% $NaHCO_3$ (aq.) in PEG was found to augment the yield of 1b by up to 39%. The replacement of $NaHCO_3$ with NaOH or KOH or LiOH or $Na_2CO_3$, $K_2CO_3$ did provide 1b in comparative yield. In view of the ineptness of a single base to bring about the desired transformation, we subsequently focused our attention towards the synergistic application of two bases. Consequently, various base combinations were explored towards the decarboxylation of cinnamic acid into stilbenes. To our fascination, an increased yield of 1b was obtained in almost all instances. For instance, the combination of NaHCO$_3$ with catalytic amount of organic bases such as triethyl amine, pyridine or piperidine had produced marginal effect as the yield of 1b was increased by up to 45-52% in these cases. Nonetheless, it was the aq. NaHCO$_3$-imidazole (cat.) combination which delivered 1b in a highest 88% yield. In our desire to further augment the yield of 1b, we reckoned to explore the dependence of yield on structural changes in the imidazole moiety. Interestingly, while methylimidazole provided 1b in an enhanced yield of 96%, histidine and 1-butyl-3-methylimidazolium chloride gave 1b in only 38% and 42% yield respectively. To reinforce our premise of synergistic action, the cinnamic acid 1a was treated with aq. methylimidazole in PEG i.e. without NaHCO$_3$, but the stilbene could be obtained in only 28% yield even after prolonged reaction times of 60 min.

In order to discern the significance of aqueous medium in bringing about the transformation of 1a to 1b, the above reaction was conducted with NaHCO$_3$ and methylimidazole in PEG under anhydrous conditions. Interestingly, the product 1b was obtained in only 64% yield, thus unequivocally demonstrating the critical role of water in bringing about the decarboxylation of 1a. Similarly reactions were performed under solvent less condition on solid supports like basic alumina, acidic alumina, neutral alumina and silica gel but the product could be obtained in low yield. In order to ascertain the efficacy of microwave, 1a was refluxed with aq. NaHCO$_3$/methylimidazole (cat.) in PEG under conventional method for 12 h and the expected stilbene was obtained in 69%.

The substrate scope of the developed method was gauged by extending the same to other optionally substituted α-phenylcinnamic acids. It was found that 2- or 4-hydroxy substitution at the aryl ring of cinnamic acid moiety is a desideratum for the decarboxylation of α-phenylcinnamic acids under given conditions. Presumably, the acetoxylated α-phenylcinnamic acids underwent deacetylation before being incorporated in the decarboxylation pathway. It was also found that the methoxylated substrate gave the expected product only in traces. Interestingly, a simultaneous hydrolysis-decarboxylation was observed in case of α-phenylcinnamic ester and product was obtained in good yield. Later on, the method was also extended towards the decarboxylation of hydroxylated cinnamic acid into the corresponding styrenes but the product could be obtained in comparatively low yield due to formation of polymeric side products. Consequent to the success with cinnamic acid derivatives, the above method was explored towards decarboxylation of aromatic acids. However, aromatic acids such as 4-hydroxy substituted phenylpropanoic acid, phenylacetic acid and benzoic acid did not undergo the above reaction, thus indicating a probable selectivity towards cinnamic acid derivatives as compared to aromatic acids. It is worth mentioning that the prevalent decarboxylation protocol involving quinoline/Cu salt does not allow the selective decarboxylation of cinnamic acid moiety in comparison to aromatic acids. In this context, the pronounced selectivity observed with Mlm/NaHCO$_3$ can be a useful synthetic tool for chemoselective decarboxylation in total synthesis of complex organic compounds including natural products.

Thus the present invention, deals with the synthesis of immensely important (E)-stilbenes in a mild and stereoselective manner. It is pertinent to mention that a secondary nonetheless useful advantage of the method lies in the one pot deacetylation—decarboxylation or debenzoylation—decarboxylation of acetoxylated/benzoylated cinnamic acids and their derivatives which could considerably simplify the synthetic strategy and subsequent workup procedures for synthesis of stilbenes and styrenes.

EXAMPLES

The following examples are given by way of illustration of the present invention and should not be construed to limit the scope of the present invention.

The starting materials 2- or 4-hydroxy substituted cinnamic acids and their derivatives can be obtained from commercial sources. Discover CEM synthesizer (300 W) monomode microwave and Kenstar multimode microwave oven (2450 MHz, 1200 Watts) were used for the reactions.

Example I

Synthesis of 4-hydroxy-3-methoxy stilbene (under monomode microwave irradiation)

A mixture of α-phenyl-4-hydroxy-3-methoxy cinnamic acid (0.0083 mol), NaHCO$_3$ (10%, 5 mL), methylimidazole (2 mL) and polyethylene glycol (5 mL) were taken in a 100 ml round bottom flask fitted with a condenser. The flask was shaken well and placed inside the microwave oven and irradiated (200 W, 180° C.) for 10 minutes in parts. After completion of reaction, water added to the reaction mixture and solid precipitate formed were filtered and washed with water to obtain pure product (yield 96%) in most of the cases or further purified in silica-gel column with ethylacetate and hexane (40-60%); solid, (m.p. 132-134° C.); $^1$H NMR (CDCl$_3$) δ 7.45 (2H, d, J=7.41 Hz), 7.32 (2H, m), 7.21 (1H, m), 7.02 (5H, m), 5.66 (1H, s), 3.89 (3H, s); $^{13}$C NMR (CDCl$_3$) δ 146.7, 145.6, 137.6, 130.0, 128.7, 127.2, 126.5, 126.2, 120.5, 114.6, 108.3 and 55.9. HREIMS data: m/z [M+H]$^+$ for C$_{15}$H$_{15}$O$_2$, calculated=227.2840; observed=227.2826.

Example II

Synthesis of 4-hydroxy-3-methoxy stilbene (under multimode microwave irradiation)

A mixture of α-phenyl-4-hydroxy-3-methoxy cinnamic acid (0.0083 mol), NaHCO$_3$ (10%, 5 mL), imidazole (2 mL) and polyethylene glycol (15 mL) were taken in a 250 mL iodine flask fitted with loose funnel at the top. The flask was shaken well and placed inside the microwave oven and irradiated (900 W) for 8 minutes in parts. After completion of reaction, the reaction mixture was worked (yield 88%) as in example I. Spectral data as given in example I.

Example III

Synthesis of 4-hydroxy-3-methoxy stilbene (under conventional conditions)

A mixture of α-phenyl-4-hydroxy-3-methoxy cinnamic acid (0.0083 mol), NaHCO$_3$ (10%, 5 mL) methylimidazole (2 mL) and ethylene glycol (15 mL) were taken in a 250 mL round bottom flask fitted with reflux condenser. The flask was shaken well and placed on the heating mental and refluxed for 12 h. After completion of reaction, the reaction mixture was worked (yield 69%) as in example I. Spectral data as given in example I.

Example IV

Synthesis of 4-hydroxy-3-methoxy stilbene (under monomode microwave irradiation with inorganic base only)

A mixture of α-phenyl-4-hydroxy-3-methoxy cinnamic acid (0.0083 mol), NaHCO$_3$ (10%, 5 mL) and polyethylene glycol (5 mL) were taken in a 100 ml round bottom flask fitted with a condenser. The flask was shaken well and placed inside the microwave oven and irradiated (200 W, 180° C.) for 10 minutes in parts. After completion of reaction, the reaction mixture was worked (yield 72%) as in example I. Spectral data as given in example I.

Example V

Synthesis of 4-vinylguaiacol (by monomode microwave irradiation method)

A mixture of Ferulic acid (0.0083 mol), KOH (10%, 3 ml), methylimidazole (1 mL) and dimethylformamide (10 ml) were taken in a 100 ml round bottom flask fitted with reflux condenser. The flask was placed inside the microwave oven and irradiated (150 W, 150° C.) for 12 minutes. The cooled mixture was poured into ice-cold water and extracted with ethyl acetate. The organic layer was washed with dil HCl, water, saturated sodium bicarbonate, brine and then organic layer dried over sodium sulphate. The solvent was evaporated under reduced pressure to obtain liquid which was purified on silica gel column chromatography using mixture of hexane and ethyl acetate (9:1 to 6:4), provided sweet and pleasant smelling viscous liquid. 64% yield; $^1$H NMR (CDCl$_3$) δ 6.90 (3H, m), 6.70 (1H, dd, J=10.90 Hz and J=17.36 Hz), 5.79 (1H, s), 5.59 (1H, d, J=17.36 Hz), 5.11 (1H, d, J=10.90 Hz), 3.83 (3H, s); $^{13}$C NMR (CDCl$_3$) δ 146.7, 145.7, 136.7, 130.3, 120.1, 114.5, 111.4, 108.1, 55.9.

Example VI

Synthesis of 4-vinylguaiacol (by multimode microwave irradiation method)

A mixture of Ferulic acid (0.0083 mol), K$_2$CO$_3$ (10%, 3 ml), imidazole (1 mL) and dimethylformamide (15 ml) were taken in a 250 ml Erlenmeyer flask fitted with a loose funnel at the top. The flask was shaken well and placed inside the microwave oven over an ice bath and irradiated for 30 minutes in parts. After completion of reaction, it was worked up and purified as in example V and provided sweet and pleasant smelling viscous liquid. 59% yield; (Spectral data as in example V)

Example VII

Synthesis of 4-vinylphenol (by multimode microwave irradiation method under solvent less conditions)

A mixture of 4-acetyloxycinnamic acid (0.0083 mol), KOH (10%, 3 ml), ammonium acetate (1 g) and basic alumina (5 g) were taken in a 250 ml Erlenmeyer flask fitted with loose funnel at the top. The flask was placed inside the microwave oven and irradiated for 10 minutes. After completion of reaction the solid mixture washed with ethyl acetate and ethyl acetate layer was washed with dil HCl, water, brine and dried over anhydrous sodium sulphate and purified on silica gel column chromatography using mixture of hexane and ethyl acetate (9:1 to 6:4) provided viscous liquid. 49% yield; $^1$H NMR (CDCl$_3$) δ 7.31 (2H, d, J=8.48 Hz), 6.81 (2H, d, J=8.48 Hz), 6.67 (1H, dd, J=17.81 and 11.30 Hz), 5.51 (1H, s), 5.2 (1H, d, J=17.81), 5.14 (1H, d, J=11.30 Hz); $^{13}$C NMR (CDCl$_3$) δ 155.5, 136.5, 130.9, 128.0, 115.8 and 112.0.

Example VIII

Synthesis of 4'-Chloro-4-hydroxy-3-methoxy stilbene (under monomode microwave irradiation)

A mixture of α-(4'-chlorophenyl)-4-acetyloxy-3-methoxy cinnamic acid (0.0083 mol), NaHCO$_3$ (10%, 5 mL) and methylimidazole (2 mL) and diethylene glycol (8 mL) were taken in a 100 ml round bottom flask fitted with a condenser. The flask was shaken well and placed inside the microwave oven and irradiated (200 W, 180° C.) for 9 minutes in parts. After completion of reaction, the reaction mixture was worked (yield 89%) as in example I; solid, (m.p. 121-124° C.); $^1$H NMR (CDCl$_3$) δ 7.35 (2H, d, J=8.48 Hz), 7.25 (2H, d, J=8.07 Hz), 6.96 (3H, m), 6.87 (2H, d, J=8.07 Hz), 5.72 (1H, s), 3.87 (3H, s); $^{13}$C NMR (CDCl$_3$) δ 146.8, 145.8, 136.1, 132.7, 129.6, 129.2, 128.8, 127.4, 125.1, 120.6, 114.6, 108.3 and 55.9. HREIMS data: m/z [M+H]$^+$ for C$_{15}$H$_{14}$O$_2$Cl, calculated=261.7229; observed=261.7228.

Example IX

Synthesis of 1-(4'-hydroxy-3'-methoxyphenyl)-2-naphthylethene (under monomode microwave irradiation)

A mixture of α-(1-naphthyl)-4-hydroxy-3-methoxy cinnamic acid (0.0083 mol), KHCO$_3$ (10%, 5 mL) and methylimidazole (2 mL) and dimethylsulphoxide (8 mL) were taken in a 100 ml round bottom flask fitted with a condenser. The flask was shaken well and placed inside the microwave oven and irradiated (200 W, 180° C.) for 10 minutes in parts. After completion of reaction, the reaction mixture was worked (yield 88%) as in example I; solid, (m.p. 83-86° C.); $^1$H NMR (CDCl$_3$) δ 8.22 (1H, d, J=7.68 Hz), 7.85 (1H, d, J=8.23 Hz), 7.77 (3H, m), 7.51 (3H, m), 7.11 (2H, m), 7.08 (1H, d, J=17.05 Hz), 6.95 (1H, d, J=8.23 Hz), 5.74 (1H, s), 3.91 (3H, S); $^{13}$C NMR (CDCl$_3$) δ 146.8, 145.8, 135.3, 133.8, 131.7, 131.4, 128.7, 127.8, 126.0, 125.8, 123.8, 123.6, 123.0, 120.6, 114.7, 108.6 and 56.0. HREIMS data: m/z [M+H]$^+$ for C$_{19}$H$_{17}$O$_2$, calculated=277.3440; observed=277.3441.

Example X

Synthesis of 4-hydroxy-3,4'-dimethoxystilbene (under monomode microwave irradiation from cinnamic esters)

A mixture of Methyl α-phenyl-4-hydroxy-3,4'-dimethoxy cinnamic ester (0.0083 mol), K$_2$CO$_3$ (10%, 5 mL) and methylimidazole (1-2 mL) and 1-butyl-3-methylimidazolium chloride (5 mL) were taken in a 100 ml round bottom flask fitted with a condenser. The flask was shaken well and placed inside the microwave oven and irradiated (200 W, 180° C.) for 10 minutes in parts. After completion of reaction, the reaction mixture was worked up (yield 78%) as in example I. solid, (m.p. 163-166° C.); $^1$H NMR (CDCl$_3$) δ 7.36 (2H, d, J=8.48 Hz), 6.94 (2H, m), 6.83 (5H, m), 5.59 (1H, s), 3.86 (3H, s), 3.75 (3H, s); $^{13}$C NMR (CDCl$_3$) δ 159.0, 146.7, 145.2, 130.3, 127.4, 126.6, 126.1, 120.1, 114.5, 114.1, 108.0, 55.9 and 55.3. HREIMS data: m/z [M+H]$^+$ for C$_{16}$H$_{17}$O$_3$, calculated=257.3103; observed=257.3149.

Example XI

Synthesis of 2-Hydroxy-3-methoxystilbene (under monomode microwave irradiation)

A mixture of α-phenyl-2-benzoyl-3-methoxy cinnamic acid (0.0083 mol), KHCO$_3$ (10%, 5 mL) and methylimidazole (2 mL) and 1-butyl-3-methylimidazolium chloride (5 mL) were taken in a 100 ml round bottom flask fitted with a condenser. The flask was shaken well and placed inside the microwave oven and irradiated (200 W, 180° C.) for 10 minutes in parts. After completion of reaction, the reaction mixture was worked up (yield 76%) as in example I; solid, (m.p. 85-87° C.); $^1$H NMR (CDCl$_3$) δ 7.51 (2H, d, J=7.68 Hz), 7.44 (1H, d, J=16.47 Hz), 7.38 (1H, d, J=16.47 Hz), 7.33 (1H, t, J=7.68 Hz), 7.22 (3H, m), 6.80 (1H, t, J=7.96 Hz), 6.73 (1H, d, J=7.96 Hz), 5.95 (1H, s), 3.84 (3H, s); $^{13}$C NMR (CDCl$_3$) δ 146.7, 143.5, 137.8, 129.3, 128.5, 127.3, 126.5, 123.7, 122.9, 119.5, 118.8, 109.4 and 56.0. HREIMS data: m/z [M+H]$^+$ for C$_{15}$H$_{15}$O$_2$, calculated=227.2840; observed=227.2830.

Example XII

Synthesis of 2-hydroxy styrene (by monomode microwave irradiation method)

A mixture of 2-hydroxycinnamic acid or coumarin (2H-1-Benzopyran-2-one) (0.0083 mol), LiOH (10%, 4 mL), imidazole (1 mL) and dimethylsulphoxide were taken in a 100 ml round bottom flask fitted with reflux condenser. The flask was placed inside the microwave oven and irradiated (200 W, 180° C.) for 5-8 minutes. After completion of reaction, it was worked up and purified as in example V and provided viscous liquid. 58% yield; $^1$H NMR (CDCl$_3$) δ 7.40 (1H, d, J=7.67 Hz), 7.14 (1H, m), 6.95 (2H, m), 6.80 (1H, d, J=8.07 Hz), 5.78 (1H, d, J=17.10 Hz), 5.37 (1H, d, J=11.20 Hz), 5.01 (1H, s); $^{13}$C NMR (CDCl$_3$) δ 153.1, 132.2, 129.8, 128.4, 125.6, 121.8, 116.7 and 116.4.

Example XIII

Synthesis of 3,4-dimethoxy styrene (by monomode microwave irradiation method)

A mixture of 3,4-dimethoxycinnamic acid (0.0083 mol), KOH (10%, 5 ml), methylimidazole (1 mL) and polyethylene glycol (5 ml) were taken in a 100 ml round bottom flask fitted with reflux condenser. The flask was placed inside the microwave oven and irradiated (200 W, 200° C.) for 15 minutes. After completion of reaction, it was worked up and purified as in example V and provided a solid (m.p. 110-114° C.); $^1$H NMR (CDCl$_3$) δ 7.01 (2H, m), 6.84 (1H, d, J=7.27 Hz), 6.63 (1H, d, J=10.80 Hz and J=16.10 Hz), 5.60 (1H, d, J=16.10 Hz), 5.15 (1H, d, J=10.80 Hz), 3.90 (1H, s), 3.87 (1H, s); $^{13}$C NMR (CDCl$_3$) δ 150.1, 149.2, 137.4, 131.2, 119.8, 112.6, 111.6, 109.7 and 55.8.

Example XIV

Synthesis of 3,4,4'-trimethoxystilbene (by monomode microwave irradiation method)

A mixture of α-(4'-methoxyphenyl-3,4-dimethoxy cinnamic acid (0.0083 mol), NaOH (10%, 5 ml), methylimidazole (2 mL) and polyethylene glycol (5 ml) were taken in a 100 ml round bottom flask fitted with reflux condenser. The flask was placed inside the microwave oven and irradiated (200 W, 180° C.) for 20 minutes. After completion of reaction, it was worked up and purified as in example I and provided a solid, (m.p. 131-134° C.); $^1$H NMR (CDCl$_3$) δ 7.38 (2H, d, J=8.51 Hz), 6.98 (2H, m), 6.86 (5H, m), 3.88 (3H, s), 3.83 (3H, s), 3.76 (3H, s); $^{13}$C NMR (CDCl$_3$) δ 159.1, 149.1, 148.6, 130.8, 130.3, 127.4, 126.4, 119.5, 114.1, 111.3, 108.6, 55.9, 55.8 and 55.3.

Example XV

Decarboxylation of 4-hydroxybenzoic acid, 4-hydroxyphenylacetic acid, 4-hydroxyphenylpropanoic acid (by monomode microwave irradiation method)

A mixture of 4-hydroxybenzoic acid (0.0129 mol), NaOH (10%, 5 ml), methylimidazole (2 mL) and polyethylene glycol (5 ml) were taken in a 100 ml round bottom flask fitted with reflux condenser. The flask was placed inside the microwave oven and irradiated (200 W, 180° C.) for 20 minutes. No reaction occurred and the substrate obtained unreacted. Similarly reaction was repeated with 4-hydroxyphenylacetic acid, 4-hydroxyphenylpropanoic acid by replacing these with benzoic acid and no reaction was observed.

THE MAIN ADVANTAGES OF THE INVENTION

The main advantage of the present invention is a process to prepare high valued 2- or 4-hydroxy substituted arylethenes like styrenes or stilbenes from corresponding acids.

1. A process to employ ecofriendly microwave technique for the preparation of 2- or 4-hydroxy substituted arylethenes.
2. A process to prepare 2- or 4-hydroxy substituted arylethenes in much shorter reaction time in minutes.
3. A process for the preparation of 2- or 4-hydroxy substituted arylethenes wherein reaction can be performed under solvent less conditions utilizing solid support.
4. A process in which monomode or multimode microwave is used for the preparation of 2- or 4-hydroxy substituted styrenes or arylethenes
5. A process in which base is selected from a group consisting of sodium hydroxide, potassium hydroxide, lithium hydroxide, sodium bicarbonate, sodium carbonate, potassium bicarbonate, potassium carbonate, ammonium acetate, imidazole, methylimidazole and the combination thereof.
6. A process in which the solid support is selected from a group consisting of a basic alumina, acidic alumina, neutral alumina, silica gel and the like.
7. A process to prepare 2- or 4-hydroxy substituted arylethenes in one pot.
8. A process for easy workup as well as purification of the product.

9. A process which utilizes less hazardous or non hazardous chemicals.
10. A process which requires cheaper chemical reagents.
11. An industrially viable process towards formation of high valued substituted 2- or 4-hydroxy substituted arylethenes.

The invention claimed is:

1. A microwave induced one pot process for the preparation of arylethenes of general formula (I),

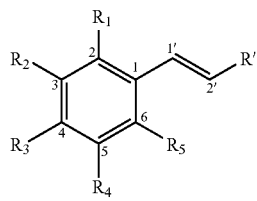

Formula I wherein $R_1$ to $R_5$ are defined as, at least one OH or acetoxy substituent among $R_1$, $R_3$, $R_5$ and rest of substituents $R_1$ to $R_5$, being H or OH or $OCH_3$ or $CH_3COO$— or halogen or nitro or combinations thereof, R'=H in case of styrenes and substituted aryl group in case of stilbenes, the said process comprising steps of:
  a) reacting 2- or 4-hydroxy substituted cinnamic acid or its derivative in the presence of a combination of organic and inorganic bases, a solid support, and a solvent under microwave irradiation for 1 min-12 hrs, wherein the organic base is imidazole or methyimidazole, and the inorganic base is selected from a group consisting of sodium hydroxide, potassium hydroxide, lithium hydroxide, sodium bicarbonate, sodium carbonate, potassium bicarbonate, and potassium carbonate;
  b) transferring the reaction mixture of step (a) and washing a residue with an organic solvent,
  c) washing the organic solution of step (b) with aqueous sodium bicarbonate or sodium carbonate followed by brine and water,
  d) drying the organic layer of step (c) over anhydrous sodium sulphate, filtering and evaporating to dryness to obtain another residue,
  e) purifying the residue of step (d) by column chromatography or recrystallization to obtain the corresponding arylethenes of general formula (I).

2. The process according to claim 1, wherein the arylethenes are prepared by decarboxylation of the cinnamic acids and their derivatives.

3. The process according to claim 2, wherein the cinnamic acids and their derivatives are selected from a group consisting of substituted cinnamic acids or α-phenyl cinnamic acids or cinnamic acid esters with at least one hydroxyl substitution unprotected or protected by acetyl, and benzyl groups at 2- or 4-position of aromatic ring.

4. The process according to claim 1, wherein the combination of inorganic and organic bases enhances a yield of the arylethenes by 25-30%.

5. The process according to claim 1, wherein the solid support is selected from a group consisting of a basic alumina, acidic alumina, neutral alumina, and silica gel.

6. The process according to claim 1, wherein the solvent wherever used is selected from a group consisting of dimethylformamide, dimethylsulfoxide, ethylene glycol, diethylene glycol, acetonitrile, acetone, methyl imidazoles, ionic liquid, water and a combination thereof.

7. The process according to claim 1, wherein the process shows a remarkable selectivity for the decarboxylation of cinnamic acid moiety in comparison to benzoic acids, phenylacetic acids, phenylpropanoic acid.

8. The process according to claim 1, wherein the mole ratio between the 2- or 4-hydroxy substituted cinnamic acid and base is ranging from 1:1 to 1:20.

9. The process according to claim 1, wherein the method is found equally workable in monomode and multimode microwave.

10. The process according to claim 1, wherein the reaction is performed in a monomode microwave operated at 200 W.

11. The process according to claim 1, wherein the microwave irradiation frequency used is 2450 Mhz.

12. The process according to claim 1, wherein the temperature attained in case of monomode microwave is in the range of about 180° C. to about 200° C.

13. The process according to claim 1, wherein the reaction is successfully performed in a domestic multimode microwave oven operated at 700 W-1500 W power level for 1-20 min.

14. The process according to claim 1, wherein the yield of arylethenes as obtained in step (a) is up to about 96%.

* * * * *